United States Patent
Williams

(10) Patent No.: US 11,191,736 B2
(45) Date of Patent: Dec. 7, 2021

(54) PHARMACEUTICAL FORMULATIONS CONTAINING CANNABIDIOL AND NICOTINE FOR TREATING SMOKELESS TOBACCO ADDICTION

(71) Applicant: CV Sciences, Inc., San Diego, CA (US)

(72) Inventor: Jonnie R. Williams, Sarasota, FL (US)

(73) Assignee: CV Sciences, Inc., San Diego, CA (US)

( * ) Notice: Subject to any disclaimer, the term of this patent is extended or adjusted under 35 U.S.C. 154(b) by 3 days.

(21) Appl. No.: 16/841,834

(22) Filed: Apr. 7, 2020

(65) Prior Publication Data
US 2020/0230077 A1 Jul. 23, 2020

Related U.S. Application Data

(62) Division of application No. 15/426,617, filed on Feb. 7, 2017, now Pat. No. 10,653,639.

(60) Provisional application No. 62/336,990, filed on May 16, 2016.

(51) Int. Cl.
| | |
|---|---|
| *A61K 9/00* | (2006.01) |
| *A61K 31/05* | (2006.01) |
| *A61K 9/68* | (2006.01) |
| *A61K 31/465* | (2006.01) |
| *A61K 9/70* | (2006.01) |

(52) U.S. Cl.
CPC ............ *A61K 31/05* (2013.01); *A61K 9/0043* (2013.01); *A61K 9/0058* (2013.01); *A61K 9/7038* (2013.01); *A61K 31/465* (2013.01)

(58) Field of Classification Search
CPC .................................................. A61K 9/0043
See application file for complete search history.

(56) References Cited

U.S. PATENT DOCUMENTS

| | | | |
|---|---|---|---|
| 8,603,440 | B2 | 12/2013 | Andersen et al. |
| 9,023,322 | B2 | 5/2015 | Van Damme et al. |
| 9,028,803 | B2 | 5/2015 | Nielsen et al. |
| 9,433,601 | B2 | 9/2016 | Van Damme et al. |
| 2002/0098264 | A1 | 7/2002 | Cherukuri et al. |
| 2003/0159702 | A1 | 8/2003 | Lindell et al. |
| 2007/0014887 | A1 | 1/2007 | Cherukuri et al. |

(Continued)

FOREIGN PATENT DOCUMENTS

| | | |
|---|---|---|
| EP | 2233134 A1 | 9/2010 |
| KR | 960005143 B1 | 4/1996 |

OTHER PUBLICATIONS

G.L. Ream et al. / Drug and Alcohol Dependence 95 (2008) 199-208. (Year: 2008).*

(Continued)

*Primary Examiner* — Benjamin J Packard
(74) *Attorney, Agent, or Firm* — Banner & Witcoff, Ltd.

(57) ABSTRACT

In one aspect, a method of treating smokeless tobacco addiction comprising administering to an individual in need thereof a pharmaceutical composition comprising nicotine, a therapeutically effective amount of cannabidiol, and a pharmaceutically acceptable vehicle therefor. In some aspects, the composition is administered transmucosally, such as in an oral dosage form or nasal spray. In other aspects, the composition is administered transdermally. In another aspect, a chewable gum contains nicotine in at least a base portion and cannabidiol in at least an outer portion thereof.

17 Claims, 2 Drawing Sheets

(56) References Cited

U.S. PATENT DOCUMENTS

| | | |
|---|---|---|
| 2009/0298929 A1 | 12/2009 | Jarho et al. |
| 2010/0236562 A1 | 9/2010 | Hearn et al. |
| 2010/0247586 A1 | 9/2010 | Hugerth et al. |
| 2010/0317729 A1 | 12/2010 | Guy et al. |
| 2014/0166028 A1 | 6/2014 | Fuisz et al. |
| 2014/0209109 A1 | 7/2014 | Larson |
| 2014/0271940 A1 | 9/2014 | Wurzer |
| 2014/0328973 A1 | 11/2014 | Nielsen |
| 2015/0057341 A1 | 2/2015 | Perry |
| 2015/0057342 A1 | 2/2015 | Koren et al. |
| 2015/0099015 A1 | 4/2015 | Tsai |
| 2015/0111999 A1 | 4/2015 | Bullus |
| 2016/0074332 A1 | 3/2016 | Tygesen et al. |
| 2017/0312261 A1 | 11/2017 | Changoer et al. |

OTHER PUBLICATIONS

Jun. 3, 20200—(JP) Notification of Reasons for Refusal—App 2018-558730—Eng Tran.

Benowitz, Neal L.; Hukkanen, Janne; and Jacob, III, Peyton, "Nicotine Chemistry, Metabolism, Kinetics and Biomarkers," Handb Exp Pharmacol. 2009; (192): 29-60. doi: 10.1007/978-3-540-69248-5_2.

Morgan, C.J., Das, R.K., Joye, A., Curran, H.V., and Kamboj, S.K., "Cannabidiol reduces cigarette consumption in tobacco smokers: Preliminary findings," Addictive behaviors 38.9 (2013): 2433-2436 http://www.sciencedirect.com/science/article/pii/S030646031300083X.

Pakhale, S., Samet, J., Folan, P., Leone, F., and White, A., "The Case for Requiring Graphic Warning Labels on Smoke Tobacco Product Packages," Public Health and Policy, AnnalsATS vol. 13, No. 3, Mar. 2016, pp. 329-333.

Benowitz, Neal L., MD, "Nicotine and Smokeless Tobacco," CA-A Cancer Journal for Clinicians, vol. 38., No. 4, Jul./Aug. 1988, pp. 244-247.

Guide to Quitting Smokeless Tobacco, American Cancer Society, 2014, 29 pages.

Sifferlin, A., Smokeless Tobacco More Toxic Than Cigarettes, Study Says, Health Public Health, Nov. 18, 2015, http://time.com/4116934/smokeless-tobacco-more-toxic-than-cigarettes-study-says/.

Leweke, F.M., Piomelli, D., Pahlisch, F., Muhl, D., Gerth, C.W., Hoyer, C., Klosterkotter, J., Hellmich, M., and Koethe, D., "Cannabidiol enhances anadamide signaling and alleviates pyschotic symptoms of schizophrenia," Translational Psychiatry (2012) 2, e94, doi: 10.1038/tp. 2012.15, 7 pages.

Szalavitz, M., Marijuana Compound Treats Schizophrenia with Few Side Effects: Clinical Trial, Time.com, May 30, 2012, 6 pages, http://healthland.time.com/2012/05/30/marijuana-compound-treats-schizophrenia-with-few-side-effects-clinical-trial/.

Guillem, K., Vouillac, C., Azar, M., Parsons, L. Koob, G., Cador, M., and Stinus, L., "Monoamine Oxidase Inhibition Dramatically Increases the Motivation to Self-Administer Nicotine in Rats," Behavioral/Systems/Cognitive, The Journal of Neuroscience, Sep. 21, 2005, 25(38):8593-8600.

Linge, R., Jimenez-Sanchez, L., Campa, L., Pilar-Cuellar, F., Vidal, R., Pazos, A., Adell, A., and Diaz, A., Cannabidiol induces rapid-acting antidepressant-like effects and ehnaces cortical 5-HT/glutamate neurotransmission: role of 5-HT1A receptors, Neuropharmacology, vol. 103, Apr. 2016, pp. 16-26, http://www.sciencedirect.com/science/article/pii/S0028390815302136.

Safety, Side Effects of Cannabidiol, Current Drug Safety, 2011, vol. 6, No. 4, 1 page.

Test of the MAO Inhibitory Properties of Cannabidiol, 3 pages.

A.W. Zuardi. Cannabidiol: from an inactive cannabinoid to a drug with wide spectrum of action. Rev Bras Psiquiatr. 2008: 30(3): 271-80.

Dorothy K. Hatsukami and Herbert H. Severson. Oral spit tobacco: addiction, prevention and treatment. Nicotine & Tobacco Research (1999) 1, 21-44.

Jul. 11, 2017—(WO) International Search Report—App PCT/US2017/030558.

Fisar, Z., "Inhibition of monoamine oxidase activity by cannabinoids," Naunyn-Schmiedeberg's Archives of Pharmacology ( 2010) vol. 381, No. 6, pp. 563-572.

Dorothy Hatsukami, Joni Jensen, Sharon Allen, Mike Grillo, and Robin Bliss, "Effects of Behavioral and Pharmacological Treatment on Smokeless Tobacco Users," Journal of Consulting and Clinical Psychology, 1996, vol. 64, No. 1, pp. 153-161.

Jan. 9, 2020—(EP) Search Report—App 17799853.1.

Morgan, Celia J.A.; Das, Ravi K.; Joye, Alyssa; Curran, H. Valerie; and Kamboj, Sunjeev K., "Cannabidiol reduces cigarette consumption in tobacco smokers: Preliminary findings" Addictive Behaviors 38 (2013) 2433-2436.

Schurr, Avital; Porath, Ofra; Krup, Margalith; and Livne, Avinoam, "The Effects of Hashish Components and Their Mode of Action on Monoamine Oxidase From The Brain," Biochemical Pharmacology, vol. 27, (1978) pp. 2513-2517.

\* cited by examiner

PHARMACEUTICAL FORMULATIONS CONTAINING CANNABIDIOL AND NICOTINE FOR TREATING SMOKELESS TOBACCO ADDICTION

CROSS-REFERENCE TO RELATED APPLICATIONS

This application is a division of U.S. application Ser. No. 15/426,617, filed Feb. 7, 2017, which claims priority under 35 U.S.C. § 119(e) to U.S. Application No. 62/336,990, filed May 16, 2016, the entire disclosures of which are hereby incorporated by reference.

BACKGROUND

Nicotine has a number of psychoactive effects on the human body such as producing an enhanced sense of well-being and relaxation and reducing anxiety and appetite. The intake of nicotine differs significantly between users of smokeless tobacco products and cigarette smokers. For example, the amount of nicotine absorption from a typical smokeless tobacco product can be four times or more than the amount absorbed from smoking a cigarette. Also, nicotine is absorbed more slowly from use of smokeless tobacco products, resulting in venous plasma levels that plateau during and even after use of the product. While cigarette smokers experience similar peak venous plasma levels as those of smokeless tobacco users, the venous plasma levels fall rapidly after smoking. See Benowitz, "Nicotine and Smokeless Tobacco," CA-A Cancer Journal for Clinicians, Vol. 38, No. 4, pp. 244-247 (1998).

Existing nicotine replacement therapy (NRT) products generally are designed to mimic nicotine levels achieved through cigarette smoking. As a result, dosing of NRT products tends to be difficult for smokeless tobacco users. See American Cancer Society, "Guide to Quitting Smokeless Tobacco," (2014). Due to the different nicotine plasma profiles associated with the use of smokeless tobacco products, as well as the failure to address other (non-nicotine) factors contributing to smokeless tobacco addiction including the anti-depressive effects of tobacco, existing NRT products to date have been largely unsuccessful in the treatment of smokeless tobacco addiction.

SUMMARY

In one aspect, a method of treating smokeless tobacco addiction comprises administering to an individual in need thereof a pharmaceutical composition comprising nicotine and a therapeutically effective amount of cannabidiol, and a pharmaceutically acceptable vehicle therefor. In some examples, the composition may be administered to the individual by transmucosal delivery, such as via a chewing gum or other oral dosage form, or a nasal spray. In other examples, the composition may be administered to the individual by transdermal delivery, such as via a transdermal patch.

In another aspect, an oral pharmaceutical dosage form comprises nicotine and a therapeutically effective amount of cannabidiol, and a pharmaceutically acceptable vehicle therefor. In some examples, a dosage form includes a core that contains nicotine and an outer portion that contains cannabidiol. In some aspects, the oral dosage form may be a chewable gum. In other aspects, the oral dosage form may be a tablet or capsule.

In another aspect, a method of making a chewing gum product comprises providing a gum base containing nicotine. The gum base is coated with cannabidiol, and microwave radiation is applied to infuse the cannabidiol into at least an outer portion of the gum base.

The combination of cannabidiol and nicotine, especially when present in certain dosage forms as described herein, was found to provide a synergistic activity that is particularly efficacious for the treatment of smokeless tobacco addiction. The combination thus presents a solution to a long felt need, as existing NRT and other therapies for smoking cessation have been largely ineffective for treating smokeless tobacco addiction.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Figure 1:
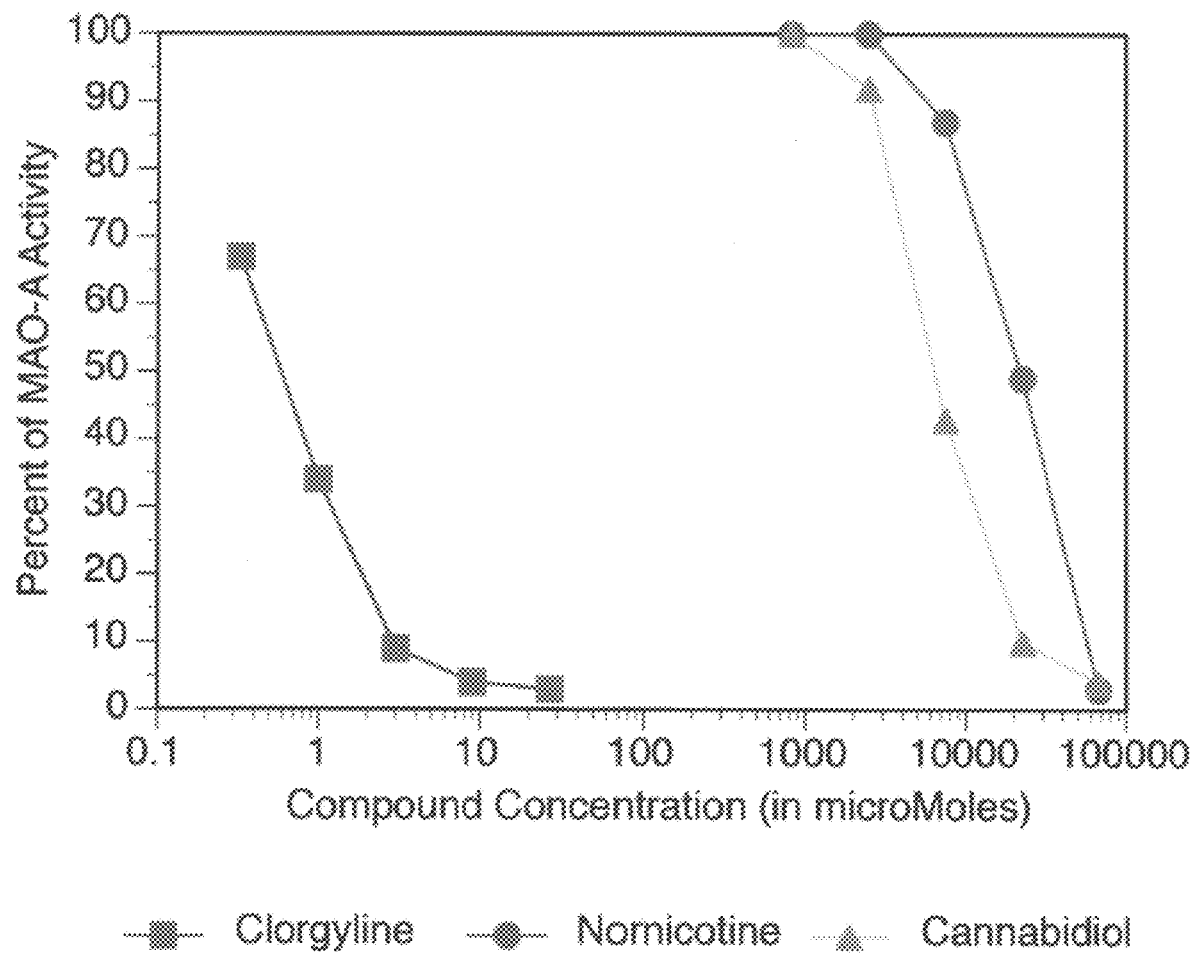
FIG. 1 is a graph showing monoamine oxidase-A (MAO-A) inhibition activity of cannabidiol.

Aspects of the present specification disclose, in part, a pharmaceutical composition. As used herein, the term "pharmaceutically acceptable composition" is synonymous with "pharmaceutical composition" and is one that includes a therapeutically effective concentration of an active ingredient to produce an intended response. A pharmaceutical composition disclosed herein may be useful for medical or veterinary applications. A pharmaceutical composition may be administered to an individual alone, or in combination with other supplementary active ingredients, agents, drugs or hormones. In general, the compositions may be administered by any suitable route, including by not limited to orally, intravenously, transdermally, subcutaneously, topically, parenterally, or a combination thereof. Non-limiting examples of suitable dosage forms that may be used include chewing gum, lozenge, transdermal patch, and nasal spray.

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" and "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition may include other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Cannabidiol and Nicotine

Cannabidiol (CBD), 2-[(1R,6R)-3-methyl-6-(1-methylethenyl)-2-cyclohexen-1-yl]-5-pentyl-1,3-benzenediol, is one of at least 113 active cannabinoids identified in cannabis. It is a major phytocannabinoid, accounting for up to 40% of the plant's extract. CBD may be prepared synthetically or extracted from appropriate natural materials, such as cannabis, using well-known techniques. CBD is prone to decomposition in the acidic conditions present the stomach; therefore, in some aspects a suitable enteric coating or the like may be used to achieve a desired delivery of the active component.

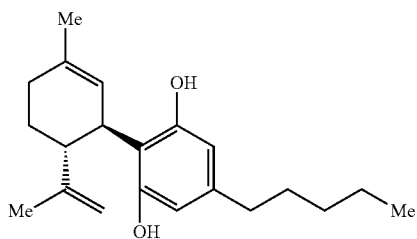 [SMILES: C=C(C)[C@@H]1CCC(C)=C[C@H]1c1c(O)cc(CCCCC)cc1O]

2-[(1R,6R)-3-methyl-6-(1-methylethenyl)-2-cyclohexen-1-yl]-5-pentyl-1,3-benzenediol Unless otherwise clear from context, references herein to "cannabidiol" or "CBD" are inclusive of both naturally occurring and synthetically-prepared compounds. The amount of CBD present in a dosage form may vary over a wide range, but by way of example often ranges from about 1 to about 300 mg, more usually from about 2 to about 250 mg, and typically from about 3 to about 200 mg, about 4 to about 180 mg, about 5 to about 160 mg, about 6 to about 140 mg, about 7 to about 120 mg, about 8 to about 100 mg, about 10 to about 80 mg, about 12 to about 60 mg, about 15 to about 50 mg, or about 20 to about 45 mg.

Although the pharmacological properties of CBD have been studied to a considerable extent in recent years, its exact mechanism of action in the human body is not fully understood. Linge et al., "Cannabidiol induces rapid-acting antidepressant-like effects and enhances cortical 5-HT/glutamate neurotransmission: role of 5-HT1A receptors," J. Neuropharm 2015.12.017, observed that despite CBD exhibiting antidepressant effects, "its potential for treating major depression has been poorly explored." CBD elsewhere has been reported as being "ineffective" for inhibiting monoamine oxidase (MAO) activity. See "Safety, Side Effects of Cannabidiol," Current Drug Safety, 2011, Vol. 6, No. 4. Notwithstanding this prior report, the present inventor made the surprising and unexpected discovery that CBD is effective for inhibiting MAO, including both MAO-A and MAO-B.

Nicotine may be prepared synthetically or extracted from appropriate natural materials, such as tobacco, using well-known techniques. Nicotine may be present in the form of a nicotine salt, nicotine free base, nicotine bound in a complex, or a suitable combination thereof. Non-limiting examples of nicotine salts include nicotine hydrochloride, nicotine dihydrochloride, nicotine monotartrate, nicotine bitartrate, nicotine sulfate, nicotine zinc chloride, nicotine salicylate, and combinations thereof. Nicotine may be bound in a complex such as ion exchange resin, e.g., a weakly acidic cation exchange resin. An example of a weakly acidic cation exchange resin is polacrilex or polymethacrilic acid (Amberlite IRP64 or Purolite C115HMR), as described in U.S. Pat. No. 3,901,248, the disclosure of which is hereby incorporated by reference in its entirety. References to "nicotine" herein are inclusive of nicotine in any of the above-described forms.

The amount of nicotine present in a dosage form may vary over a wide range, but by way of example often ranges from about 0.1 to about 10 mg, more usually from about 0.5 to about 8 mg, and typically ranges from about 1 to about 6 mg, about 2 to about 5 mg, or about 3 to about 4 mg.

The ability of CBD to inhibit monoamine oxidase makes it particularly effective for treating smokeless tobacco addiction, especially when it is appropriately co-administered with nicotine to help alleviate the "reinforcing" addictive properties of tobacco. See Guillem et al., "Monoamine Oxidase Inhibition Dramatically Increases the Motivation to Self-Administer Nicotine in Rats," J. Neurosci., 25(38): 8593-8600 (2005).

Chewing Gum

In some aspects, a pharmaceutical composition may be formulated as a chewing gum. The formulation of gum bases can vary substantially depending on the particular product to be prepared and on the desired masticatory and other sensory characteristics of the final product. By way of example, typical ranges of the gum base components include 5-80 wt. % elastomeric compounds, 5-80 wt. % natural and/or synthetic resins (elastomer plasticizers), 0-40 wt. % waxes, 5-35 wt. % softener other than waxes, 0-50 wt. % filler, and 0-5 wt. % of other ingredients such as antioxidants, colorants, and the like. The gum base may comprise about 5-95 wt. % of the total weight of the chewing gum, often from about 10-60 wt. % or from about 40-50 wt. %.

Often a buffer is used. Examples of buffers that may be used include tris buffers, amino acid buffers, carbonate, including monocarbonate, bicarbonate or sesquicarbonate, glycerinate, phosphate, glycerophosphate, acetate, gluconate or citrate of an alkali metal, such as potassium and sodium, e.g. trisodium and tripotassium citrate, or ammonium, and mixtures thereof. Other examples of buffers include acetic acid, adipic acid, citric acid, fumaric acid, glucono-δ-lactone, gluconic acid, lactic acid, malic acid, maleic acid, tartaric acid, succinic acid, propionic acid, ascorbic acid, phosphoric acid, sodium orthophosphate, potassium orthophosphate, calcium orthophosphate, sodium diphosphate, potassium diphosphate, calcium diphosphate, pentasodium triphosphate, pentapotassium triphosphate, sodium polyphosphate, potassium polyphosphate, carbonic acid, sodium carbonate, sodium bicarbonate, potassium carbonate, calcium carbonate, magnesium carbonate, magnesium oxide, or any combination thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect. The amount of buffer may range from 0 to about 15% and often ranges from about 0.5 to about 10% based on the total weight of the chewing gum.

Elastomers may be used to provide a rubbery, cohesive nature to the gum. Elastomers suitable for use in the gum base and gum may include natural or synthetic types. Elastomer plasticizers may be used to vary the firmness of the gum base. Their specificity on elastomer inter-molecular chain interaction (plasticizing) along with their varying softening points cause varying degrees of finished gum firmness and compatibility when used in base. This may provide more elastomeric chain exposure to the alkane chains of the waxes.

The elastomers employed in the gum base may vary depending upon various factors such as the type of gum base desired, the texture of gum formulation desired and the other components used in the formulation to make the final chewing gum product. The elastomer may be any water-insoluble polymer known in the art, and includes those gum polymers utilized for chewing gums and bubble gums. For example, polymers suitable for use in gum bases include, without limitation, natural substances (of vegetable origin) such as chicle gum, natural rubber, crown gum, nispero, rosidinha, jelutong, perillo, niger gutta, tunu, balata, gutta-percha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to the invention and may be natural rosin esters, often referred to as ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

Resins may be selected from terpene resins, such as those derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerized rosins, pentaerythritol esters of partially hydrogenated rosins, methyl esters of rosins, partially hydrogenated methyl esters of rosins or pentaerythritol esters of rosins and combinations thereof.

Other chewing gum ingredients may be selected from bulk sweeteners, flavors, dry-binders, tableting aids, anti-caking agents, emulsifiers, antioxidants, enhancers, absorption enhancers, buffers, high intensity sweeteners, softeners, colors, and combinations thereof. Non-limiting examples of emulsifiers include cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, and combinations thereof. The amount of emulsifiers often ranges from about 0.1% to about 25 wt. % based on the total weight of the chewing gum.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes. The compatibility of gum bases made using normal-alkanic waxes is less when compared to gum bases made with iso-alkanic waxes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm$^2$/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm$^2$/s (at 100° C.) and the combined number average molecular weight is >600 g/mole. Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. Any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, such as completely or partially hydrogenated vegetable oils or completely or partially hydrogenated animal fats.

Antioxidants prolong shelf life and storage of gum base, finished gum or their respective components including fats and flavor oils. Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

A chewing gum may include other conventional components such as sweeteners, including bulk sweeteners, sugar sweeteners, sugar-substitute sweeteners, artificial sweeteners, high-intensity sweeteners, or a combination thereof. Bulk sweeteners may constitute from about 5 to about 95% by weight of the chewing gum, more typically about 20 to about 80% by weight, about 30 to 70%, or about 30 to 60% by weight of the gum.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. Non-limiting examples of high intensity sweeteners include sucralose, aspartame, salts of acesulfame, alitame, saccharin and its salts, cyclamic acid and its salts, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. The active level of artificial sweetener may vary from about 0.001 to about 8% by weight, and often ranges from about 0.02 to about 8% by weight. When carriers used for encapsulation are included, the usage level of the encapsulated sweetener will be proportionately higher. Combinations of sugar and/or non-sugar sweeteners may be used if desired.

A chewing gum and/or gum base may include one or more fillers/texturizers, such as magnesium and calcium carbonate, sodium sulfate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

A number of other well-known chewing gum components may be present, including but not limited to waxes, fats, softeners, fillers, flavors, anti-oxidants, emulsifiers, coloring agents, binding agents and acidulates. The chewing gum may be provided with an outer coating, such as a hard coating, soft coating, edible film-coating, or any combination thereof.

In some aspects, nicotine is compounded along with other components of the gum base such that nicotine is substantially uniformly contained in the gum base. Nicotine or a nicotine complex may be provided on an adsorbent such as finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof. Nicotine may be encapsulated to provide a desired controlled or sustained release thereof. An example of a chewing gum that provides for sustained release of nicotine is described in U.S. 2007/0014887, the disclosure of which is hereby incorporated by reference.

In some aspects, a gum base containing nicotine and the other components is first compounded, and then CBD is infused into an outer portion of the chewing gum. Alternatively, CBD may be compounded with nicotine and the other components such that CBD and nicotine are each substantially uniformly contained in the gum base.

In one technique, CBD is applied to the exterior of a preformed gum base and microwave radiation is applied under conditions sufficient to infuse the CBD into the outer portion of the gum base. The microwave radiation energizes water molecules present in the gum base which allows the larger CBD molecules to be absorbed through the surface and into an outer portion of the gum base. The resulting chewing gum may provide a rapid release of CBD when first placed in the mouth and a sustained release of nicotine, for example, as the individual begins to chew the gum.

A similar release profile may be achieved via an oral dosage form such as a tablet, capsule, or the like. For example, a tablet may have a core layer containing nicotine to provide a sustained release thereof, and an outer layer containing CBD to provide an immediate release thereof. Other combinations are possible. For example, one or both of the layers may contain both CBD and nicotine so that the respective active component(s) is released in both an immediate- and a sustained release manner.

Alternative Formulations

As an alternative to oral dosage forms such as chewing gums, CBD and nicotine may be provided in other delivery vehicles such as a nasal spray or transdermal patch for transmucosal or transdermal delivery of the active components, respectively. The details of such delivery vehicles are well-known to persons skilled in the art and form no part of the present invention. For example, U.S. 2010/0236562, the disclosure of which is hereby incorporated by reference, discloses a pressurized container containing nicotine, oxygen, a propellant, and other components which is designed to deliver nicotine by inhalation spray. U.S. Pat. No. 5,948,433, the disclosure of which is hereby incorporated by reference, discloses an example of a transdermal patch having a backing layer, a liner layer, and a drug-containing adhesive layer disposed between the backing layer and the liner layer.

As used herein, the term "treating," refers to reducing or eliminating in an individual a clinical symptom of smokeless tobacco addiction. For example, the term "treating" can mean reducing one or more symptoms of smokeless tobacco addiction by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more. The symptoms associated with smokeless tobacco addiction are well known and can be determined by a person of ordinary skill in the art. Those of skill in the art will know the appropriate symptoms or indicators associated with smokeless tobacco addiction and will know how to determine if an individual is a candidate for treatment as disclosed herein.

Dosing can be single dosage or cumulative (serial dosing), and can be readily determined by one skilled in the art. The timing of administration can vary from individual to individual, depending upon such factors as the severity of an individual's symptoms. For example, an effective dose of a pharmaceutical composition disclosed herein can be administered to an individual once or more daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

A pharmaceutical composition disclosed herein may be administered to an individual in combination with other therapeutic compounds to increase the overall therapeutic effect of the treatment. The use of multiple compounds to treat an indication can increase the beneficial effects while reducing the presence of side effects. In some examples, CBD and nicotine are co-administered without administering another monoamine oxidase inhibitor (MAOI).

Various modifications may be made without departing from the spirit or scope of the present invention. For example, although the pharmaceutical compositions disclosed herein are formulated for use in treating smokeless tobacco addiction, it should be recognized that the compositions also may be effective for use in smoking cessation.

The following examples illustrate but do not limit the scope of the disclosure set forth herein.

Example 1

This example illustrates preparing a chewing gum containing nicotine and cannabidiol (CBD). Commercially available Nicorette® gum containing 4 mg nicotine per dose was used as a nicotine-containing gum base. Each piece of gum was coated with 50 mg of CBD. Several of the coated gum pieces were placed in a microwave oven. Microwave radiation was then applied at the high setting for a brief period during which the CBD infused into the outer surface of the gum pieces.

Example 2

This example describes experiments for determining monoamine oxidase (MAO) inhibition activity for cannabidiol. MAOs are enzymes located on the outer membrane of mitochondria and are involved in the catabolism of monoamine neurotransmitters. There are two well-characterized isoenzymes: MAO-A, which predominantly catabolizes serotonin and norepinephrine, and MAO-B, which preferentially catabolizes benzylamine and phenylethylamine. Dopamine and tyramine are metabolized by both isoforms.

To detect the activity of MAO, a luminescent method (MAO-Glo Assay kit, from Promega, Cat #V1401) was used. In this method, a MAO substrate (a derivative of beetle luciferin provided in the kit) is mixed with the compound to be tested (in this case, myosmine and control compounds). Then, the MAO-A or MAO-B enzyme is added to the mixture and incubated with the reaction for 1 hour at room temperature. The MAO enzymes, if not inhibited by the test compound, will convert the substrate into methyl ester luciferin. Finally, a luciferin detection reagent (provided by the kit) is added (20 minutes at room temperature) to stop the MAO reaction and convert methyl ester luciferin into D-luciferin. D-luciferin reacts with luciferase to produce a luminescent signal, which is directly proportional to the D-luciferin concentration and thus the MAO activity: the greater the amount of light produced the higher the activity of MAO. The luminescent signal is measured and recorded using a luminometer.

As shown in FIG. 1, cannabidiol was found to be a potent inhibitor of MAO-A, in fact to an even greater extent than nornicotine (values appearing more leftward in FIG. 1 indicate a higher potency). At a concentration of 7.5 mM (7,500 micromolar), CBD inhibited approximately 50% of the MAO-A activity. The MAO-A inhibition activity for the positive control, clorgyline, can be seen in the left-hand portion of FIG. 1.

Figure 2:
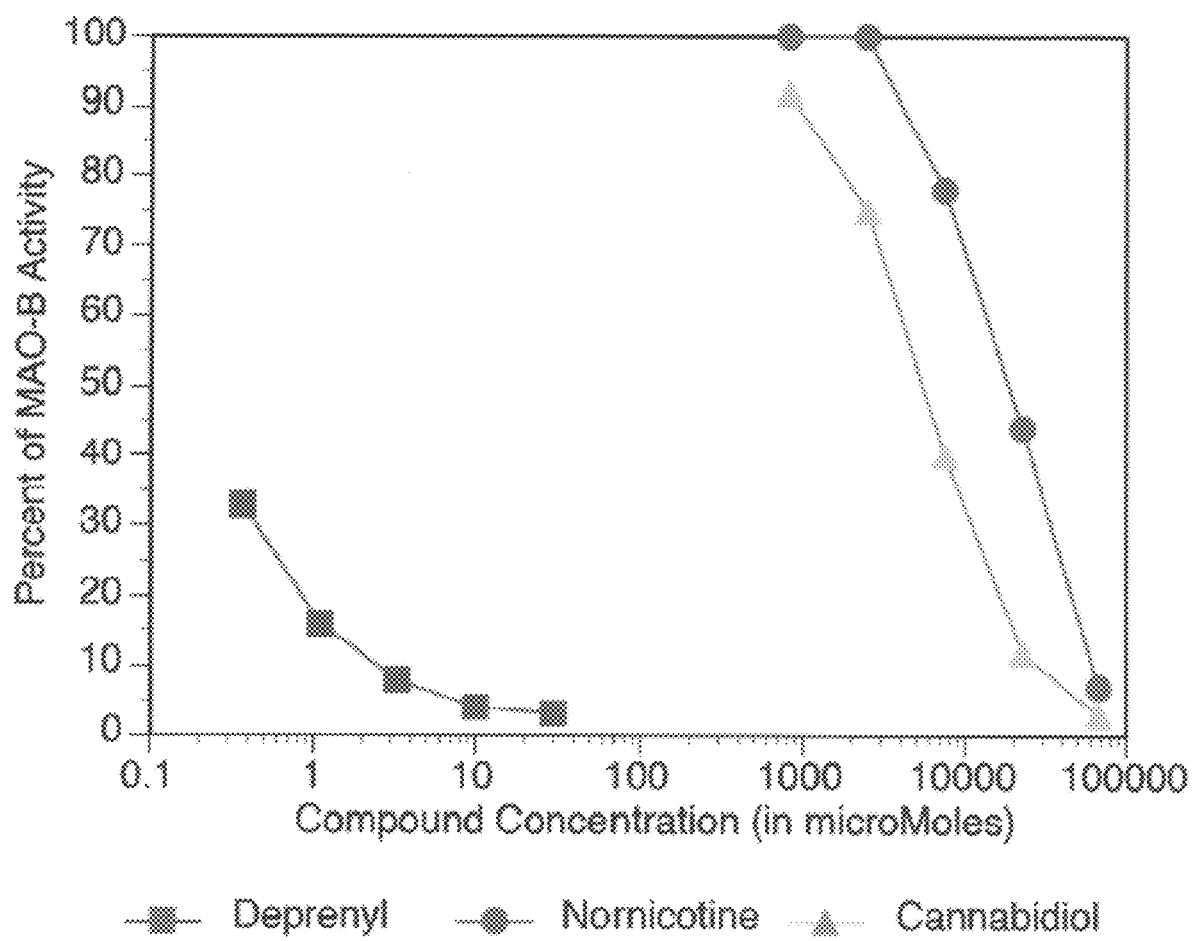
FIG. 2 is a graph showing monoamine oxidase-B (MAO-B) inhibition activity of cannabidiol.

FIG. 2 shows that CBD also inhibits MAO-B activity, although to a lesser extent than MAO-A activity. At a concentration of 7.5 mM (7,500 micromolar), CBD inhibited approximately 30% of the MAO-B activity. The MAO-B inhibition activity for the positive control, deprenyl, can be seen in the left-hand portion of FIG. 2.

Example 3

This example illustrates the treatment of an individual who was a habitual user of smokeless tobacco products for more than 20 years. The individual previously had several unsuccessful attempts to quit his use of smokeless tobacco products, including nicotine replacement therapy and even hypnosis.

The individual began daily use of the chewing gum described in Example 1 at periodic intervals during each day to satisfy cravings. The individual ceased the use of tobacco products immediately upon beginning treatment. Following eight weeks of treatment, the individual still had not used tobacco products.

Example 4

This example reports the results of a trial involving a group of ten individuals who were habitual and chronic users of smokeless tobacco products. Each of the ten individuals was given a supply of the chewing gum as described in Example 1 and instructed to use the gum as often as needed over a period of 24 hours. At the conclusion of this period, all of the subjects (10/10) reported that they used the chewing gum in lieu of the smokeless tobacco products they normally would have consumed; and all of the subjects (10/10) reported that the chewing gum was effective to significantly block cravings for smokeless tobacco.

While particular embodiments have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. An oral pharmaceutical dosage form comprising from about 0.1 to about 10 mg of nicotine, from about 1 to about 300 mg of cannabidiol, and a pharmaceutically acceptable vehicle therefor.

2. The oral pharmaceutical dosage form of claim 1 which is a chewing gum.

3. The oral pharmaceutical dosage form of claim 2 which contains nicotine in at least a base portion and cannabidiol in at least an outer portion thereof.

4. The oral pharmaceutical dosage form of claim 3 which contains from about 1 to about 5 mg of nicotine and from about 5 to about 200 mg of cannabidiol.

5. The oral pharmaceutical dosage form of claim 4 which contains from about 1 to about 4 mg of nicotine and from about 6 to about 180 mg of cannabidiol.

6. The oral pharmaceutical dosage form of claim 5 which contains from about 2 to about 4 mg of nicotine and from about 7 to about 160 mg of cannabidiol.

7. The oral pharmaceutical dosage form of claim 6 which contains from about 3 to about 4 mg of nicotine and from about 8 to about 140 mg of cannabidiol.

8. The oral pharmaceutical dosage form of claim 7 which contains from about 10 to about 100 mg of cannabidiol.

9. The oral pharmaceutical dosage form of claim 8 which contains from about 15 to about 50 mg of cannabidiol.

10. The oral pharmaceutical dosage form of claim 1 which does not contain a monoamine oxidase inhibitor other than cannabidiol.

11. A pharmaceutical dosage form comprising from about 1 to about 4 mg of nicotine, from about 8 to about 100 mg of cannabidiol, and a pharmaceutically acceptable vehicle therefor.

12. The pharmaceutical dosage form of claim 11 which comprises an oral dosage form.

13. The pharmaceutical dosage form of claim 12 wherein the oral dosage form comprises a tablet or capsule.

14. The pharmaceutical dosage form of claim 11 which comprises a nasal spray.

15. The pharmaceutical dosage form of claim 12, wherein the oral dosage form comprises a core layer containing nicotine and an outer layer containing cannabidiol.

16. The pharmaceutical dosage form of claim 15 which contains from about 2 to about 4 mg of nicotine and from about 10 to about 80 mg of cannabidiol.

17. The pharmaceutical dosage form of claim 16 which contains from about 3 to about 4 mg of nicotine and from about 15 to about 50 mg of cannabidiol.

* * * * *